(12) United States Patent
Smits et al.

(10) Patent No.: US 9,402,607 B2
(45) Date of Patent: Aug. 2, 2016

(54) IMPEDANCE GUIDED TUNNELING TOOL

(71) Applicant: Medtronic, Inc., Minneapolis, MN (US)

(72) Inventors: Karel F. A. A. Smits, Munstergeleen (NL); Jean Joseph Gerardus Rutten, Bocholtz (NL); Mark Lazeroms, Vroenhoven-Riemst (BE)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/321,091

(22) Filed: Jul. 1, 2014

(65) Prior Publication Data

US 2014/0316429 A1 Oct. 23, 2014

Related U.S. Application Data

(62) Division of application No. 12/262,560, filed on Oct. 31, 2008, now abandoned.

(51) Int. Cl.
| | | |
|---|---|---|
| A61B 5/05 | (2006.01) | |
| A61B 17/02 | (2006.01) | |
| A61N 1/04 | (2006.01) | |
| A61N 1/05 | (2006.01) | |
| A61B 19/00 | (2006.01) | |
| A61B 17/34 | (2006.01) | |
| A61B 17/00 | (2006.01) | |
| A61B 17/32 | (2006.01) | |

(52) U.S. Cl.
CPC .................. *A61B 17/02* (2013.01); *A61B 19/46* (2013.01); *A61N 1/046* (2013.01); *A61N 1/05* (2013.01); *A61N 1/0504* (2013.01); *A61B 17/3468* (2013.01); *A61B 2017/00026* (2013.01); *A61B 2017/320044* (2013.01); *A61B 2017/320056* (2013.01); *A61B 2019/462* (2013.01)

(58) Field of Classification Search
CPC ........... A61B 18/1482; A61B 17/3468; A61B 17/3403; A61B 5/061; A61B 5/063; A61B 5/068; A61B 17/02; A61N 1/046; A61N 1/0504
USPC ....................................................... 600/547
See application file for complete search history.

(56) References Cited

U.S. PATENT DOCUMENTS

| | | |
|---|---|---|
| 3,224,433 A | 12/1965 | Von Dalebor |
| 5,271,413 A | 12/1993 | Dalamagas et al. |
| 5,300,106 A | 4/1994 | Dahl et al. |

(Continued)

FOREIGN PATENT DOCUMENTS

| | | |
|---|---|---|
| EP | 1462141 | 9/2004 |
| WO | 9428809 | 12/1994 |

(Continued)

OTHER PUBLICATIONS

Final Office Action mailed Jan. 13, 2012 in U.S. Appl. No. 12/262,560.

(Continued)

*Primary Examiner* — Adam J Eiseman
*Assistant Examiner* — Yasmeen S Warsi

(57) ABSTRACT

A system includes a first electrode at a tip of a tunneling tool and a second electrode. The system includes a circuit configured to determine whether the tip of the tunneling tool is within subcutaneous fat tissue or muscle tissue of a patient based on a measurement of an impedance between the first electrode and the second electrode.

16 Claims, 6 Drawing Sheets

(56) References Cited

U.S. PATENT DOCUMENTS

| | | |
|---|---|---|
| 6,584,348 B2 | 6/2003 | Glukhovsky |
| 6,709,380 B2 | 3/2004 | Green et al. |
| 2004/0204734 A1 | 10/2004 | Wagner et al. |
| 2004/0204735 A1 | 10/2004 | Shiroff et al. |
| 2005/0288566 A1 | 12/2005 | Levendusky et al. |
| 2007/0027449 A1* | 2/2007 | Godara .............. A61B 18/1482 606/41 |
| 2007/0060832 A1 | 3/2007 | Levin |
| 2007/0203553 A1 | 8/2007 | Smits |
| 2008/0119846 A1 | 5/2008 | Rioux |
| 2008/0183230 A1 | 7/2008 | Kemmelmueller et al. |
| 2009/0192404 A1 | 7/2009 | Ortiz et al. |

FOREIGN PATENT DOCUMENTS

| | | |
|---|---|---|
| WO | 2009019707 | 2/2009 |
| WO | 2010/014375 | 2/2010 |

OTHER PUBLICATIONS

Office Action mailed Sep. 26, 2011 in U.S. Appl. No. 12/262,560.
PCT Notification of Transmittal of the International Search and the Written Opinion of the International Searching Authority, PCT/US2009/060741, International filing date Oct. 15, 2009.

* cited by examiner

IMPEDANCE GUIDED TUNNELING TOOL

CROSS-REFERENCE TO RELATED APPLICATIONS

This Utility Patent Application is a divisional application of U.S. Ser. No. 12/262,560, filed Oct. 31, 2008, which is incorporated herein by reference.

BACKGROUND

A subcutaneous device, such as a coil electrode for an implantable cardioverter-defibrillator (ICD), is typically implanted in a patient while the patient is lying supine on his or her back. The subcutaneous device is implanted using a tunneling tool that provides enough stiffness and pushability to create a space between the subcutaneous and muscular plane. With the patient on his or her back, it is difficult for a physician to maneuver a tunneling tool around the curvature of the posterior axilla to continue tunneling from the axilla to the spine.

There are two major potential problems that a physician may encounter while implanting a subcutaneous device using a tunneling tool. The first problem includes the tunneling tool turning inward between the ribs and into muscle and potentially creating a pneumothorax. The second problem includes the tunneling tool turning outward and potentially puncturing the skin. Some physicians will have a non-sterile scrub nurse put a hand under the patient's back to help guide the tunneling tool and to give the skin support so the tunneling tool does not penetrate the skin. Other physicians will use x-ray or other suitable imaging systems to help guide the tunneling tool.

For these and other reasons, there is a need for the present invention.

SUMMARY

One embodiment provides a system. The system includes a first electrode at a tip of a tunneling tool and a second electrode. The system includes a circuit configured to determine whether the tip of the tunneling tool is within subcutaneous fat tissue or muscle tissue of a patient based on a measurement of an impedance between the first electrode and the second electrode.

DETAILED DESCRIPTION

Figure 1:
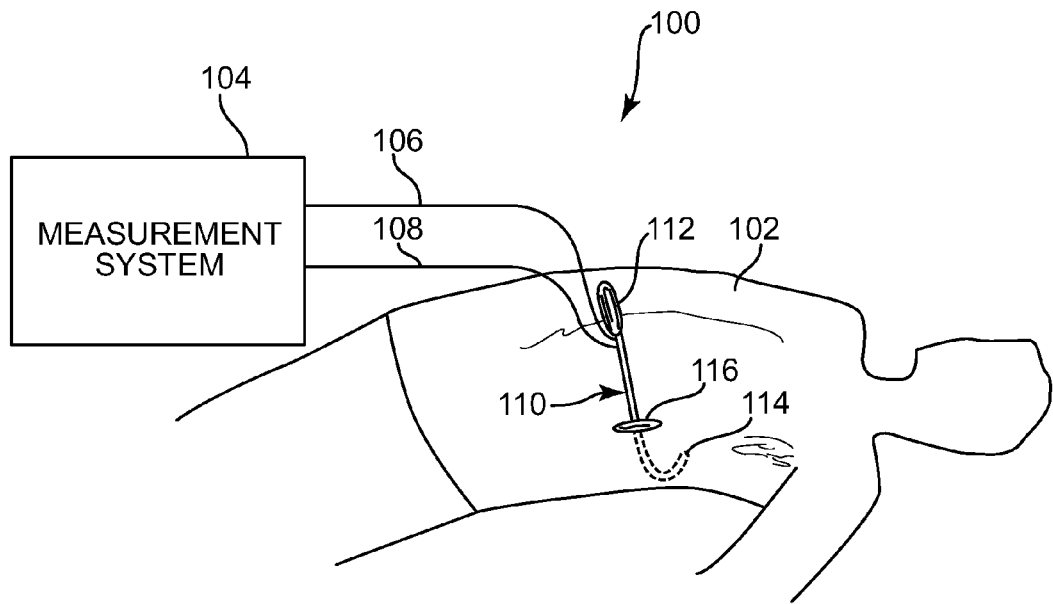
FIG. 1 is a diagram illustrating one embodiment of a system using a tunneling tool to place a subcutaneous device in a patient.

FIG. 1 is a diagram illustrating one embodiment of a system 100 using a tunneling tool 110 to place a subcutaneous device in a patient 102. To begin, patient 102 lies down on an operating table. A physician makes a subcutaneous pocket incision at 116 and inserts tunneling tool 110 into incision 116. As the physician advances tunneling tool 110 via handle 112, the tunneling tool creates a space between the subcutaneous and muscular plane in patient 102. The physician continues to advance tunneling tool 110 until the tip 114 of tunneling tool 110 is at the desired location for placing the subcutaneous device.

Measurement system 104 assists the physician in advancing tunneling tool 110 to the desired location for placing the subcutaneous device. Measurement system 104 is electrically coupled to a first electrode on the distal tip 114 of tunneling tool 110 through signal path 106. Measurement system 104 is electrically coupled to a second electrode spaced apart from the first electrode proximal distal tip 114 through signal path 108. Measurement system 104 measures the impedance between the first electrode and the second electrode. The impedance measurement indicates whether tip 114 of tunneling tool 110 is within subcutaneous fat tissue, within skin tissue, or within muscle tissue of patient 102. The physician can use the impedance measurement while guiding tunneling tool 110 to the desired location to keep tunneling tool 110 within the subcutaneous fat tissue of the patient. By monitoring the impedance measurement, if skin tissue or muscle tissue is encountered while advancing tunneling tool 110, the physician can make a correction to the tunneling tool path and prevent creating a pneumothorax and/or puncturing the skin.

The resistivity of muscle tissue is approximately 500 ohm-cm and the resistivity of subcutaneous fat tissue is approximately 2500 ohm-cm. Therefore, the impedance of subcutaneous fat tissue is approximately five times greater than the impedance of muscle tissue. As such, in one embodiment, measurement system 104 is configured to provide a visual and/or audible indication in response to a sudden change in impedance, which indicates that tip 114 of tunneling tool 110 has moved from one tissue type to another tissue type.

Figure 2:
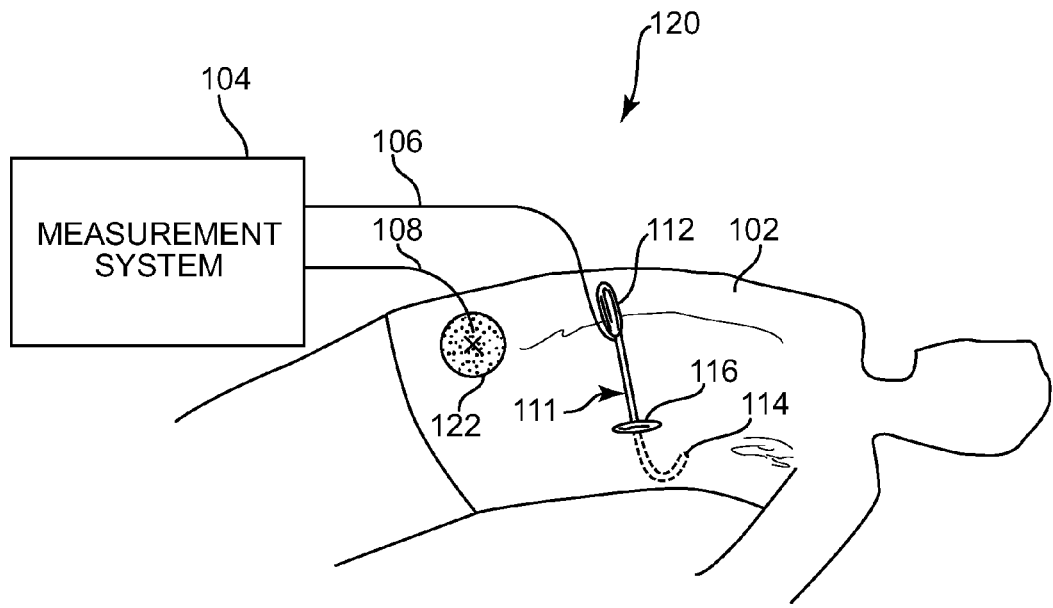
FIG. 2 is a diagram illustrating another embodiment of a system using a tunneling tool to place a subcutaneous device in a patient.

FIG. 2 is a diagram illustrating another embodiment of a system 120 using a tunneling tool 111 to place a subcutaneous device in a patient 102. System 120 is similar to system 100 previously described and illustrated with reference to FIG. 1, except that in system 120, the second electrode 122 is attached to the patient's skin. Second electrode 122 is attached to the patient's skin at any suitable location on the patient's body. In one embodiment, a conductive gel, adhesive, or other suitable material is applied to second electrode 122 before second electrode 122 is attached to the patient's skin. Measurement system 104 is electrically coupled to second electrode 122 through signal path 108. Second electrode 122 is larger than the first electrode at tip 114 of tunneling tool 111 such that the majority of the measured impedance is due to the transition from the first electrode to the tissue in which the first electrode is situated.

Measurement system 104 assists the physician in advancing tunneling tool 111 to the desired location for placing the subcutaneous device. Measurement system 104 measures the impedance between the first electrode at tip 114 of tunneling tool 111 and second electrode 122. The impedance measurement indicates whether tip 114 of tunneling tool 111 is within subcutaneous fat tissue, within skin tissue, or within muscle tissue of patient 102. The physician can use the impedance measurement while guiding tunneling tool 111 to the desired location to keep tunneling tool 111 within the subcutaneous fat tissue of the patient. By monitoring the impedance measurement, if skin tissue or muscle tissue is encountered while advancing tunneling tool 111, the physician can make a correction to the tunneling tool path and prevent creating a pneumothorax and/or puncturing the skin.

Figure 3:
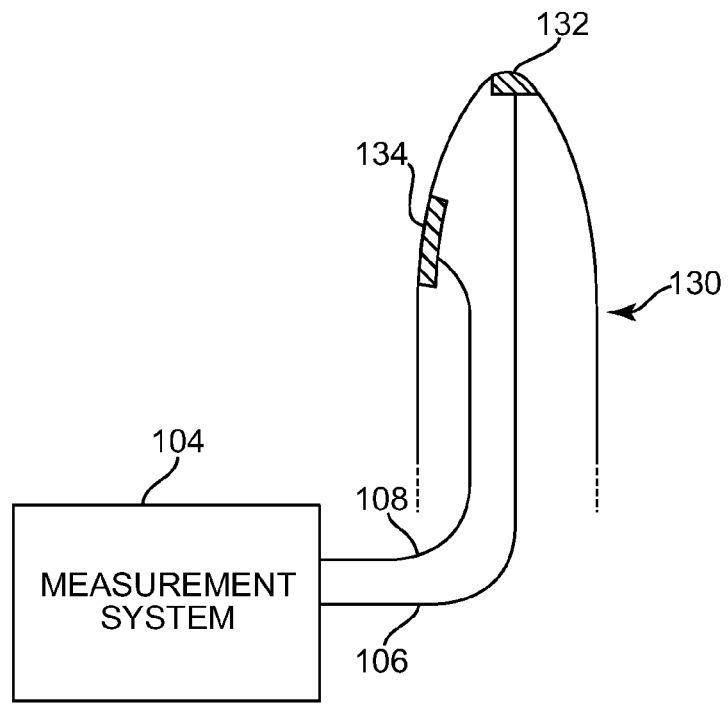
FIG. 3 is a diagram illustrating one embodiment of a tunneling tool for guiding the placement of a subcutaneous device.

FIG. 3 is a diagram illustrating one embodiment of a tunneling tool 130 for guiding the placement of a subcutaneous device. In one embodiment, tunneling tool 130 is used for tunneling tool 110 previously described and illustrated with reference to FIG. 1. Tunneling tool 130 includes a first electrode 132 and a second electrode 134. First electrode 132 is at the distal tip of tunneling tool 130. Second electrode 134 is a little more proximal on tunneling tool 130 than first electrode 132 and extends around a portion of tunneling tool 130. First electrode 132 is electrically coupled to measurement system 104 through signal path 106. Second electrode 134 is electrically coupled to measurement system 104 through signal path 108.

The impedance between first electrode 132 and second electrode 134 measured by measurement system 104 is different when the tip of tunneling tool 130 is situated within subcutaneous fat tissue than when the tip of tunneling tool 130 is situated within muscle tissue. A physician can monitor the measured impedance while advancing tunneling tool 130 within a patient to guide the physician in keeping the tip of the tunneling tool within the subcutaneous fat tissue of the patient.

Figure 4:
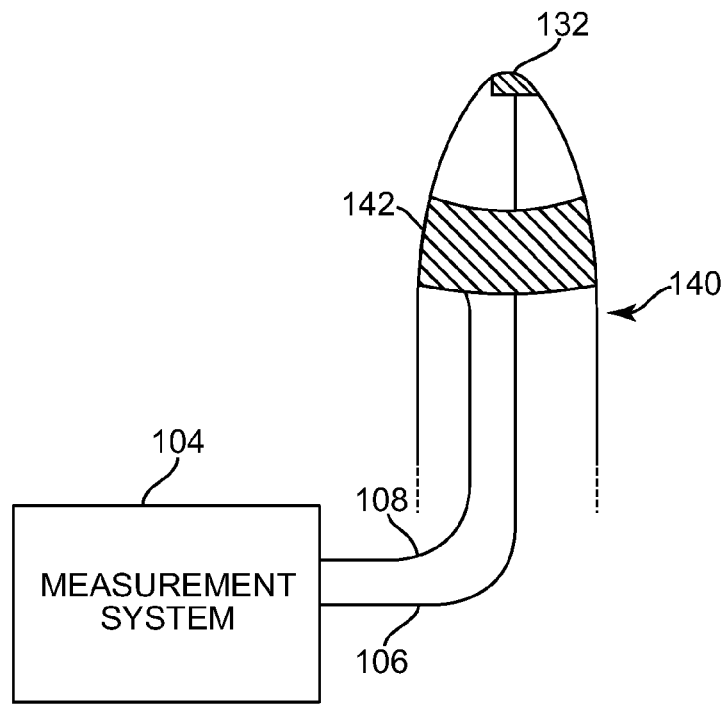
FIG. 4 is a diagram illustrating another embodiment of a tunneling tool for guiding the placement of a subcutaneous device.

FIG. 4 is a diagram illustrating another embodiment of a tunneling tool 140 for guiding the placement of a subcutaneous device. In one embodiment, tunneling tool 140 is used for tunneling tool 110 previously described and illustrated with reference to FIG. 1. Tunneling tool 140 includes a first electrode 132 and a second electrode 142. First electrode 132 is at the distal tip of tunneling tool 140. Second electrode 142 is a little more proximal on tunneling tool 140 than first electrode 132 and extends all the way around tunneling tool 140 to provide a ring electrode. First electrode 132 is electrically coupled to measurement system 104 through signal path 106. Second electrode 142 is electrically coupled to measurement system 104 through signal path 108.

The impedance between first electrode 132 and second electrode 142 measured by measurement system 104 is different when the tip of tunneling tool 140 is situated within subcutaneous fat tissue than when the tip of tunneling tool 140 is situated within muscle tissue. A physician can monitor the measured impedance while advancing tunneling tool 140 within a patient to guide the physician in keeping the tip of the tunneling tool within the subcutaneous fat tissue of the patient.

Figure 5:
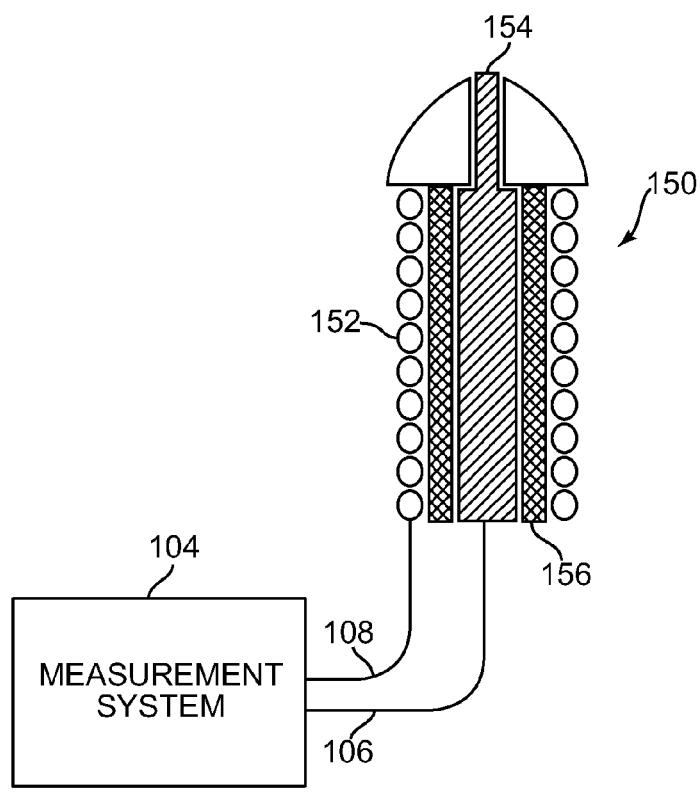
FIG. 5 is a diagram illustrating one embodiment of a lead for guiding the placement of the lead.

FIG. 5 is a diagram illustrating one embodiment of a lead 150 for guiding the placement of the lead. In one embodiment, lead 150 is used in place of tunneling tool 110 previously described and illustrated with reference to FIG. 1. Lead 150 includes a coil 152 and a central lumen to receive insertion of a stylet 154 within lead 150. Coil 152 is electrically isolated from stylet 154 by insulation material 156. Stylet 154 assists in advancing lead 150 during tunneling within a patient. Once lead 150 is positioned at a desired site within the patient, stylet 154 is removed from lead 150.

Stylet 154 provides a first electrode and is electrically coupled to measurement system 104 through signal path 106. Coil 152 provides a second electrode and is electrically coupled to measurement system 104 through signal path 108. The impedance between the tip of stylet 154 and coil 152 measured by measurement system 104 is different when lead 150 is situated within subcutaneous fat tissue than when lead 150 is situated within muscle tissue. A physician can monitor the measured impedance while advancing lead 150 within a patient to guide the physician in keeping the lead within the subcutaneous fat tissue of the patient. In one embodiment, once the lead is placed, a physician can check the measured impedance to verify that the lead is placed in subcutaneous fat tissue and not in muscle tissue.

Figure 6:
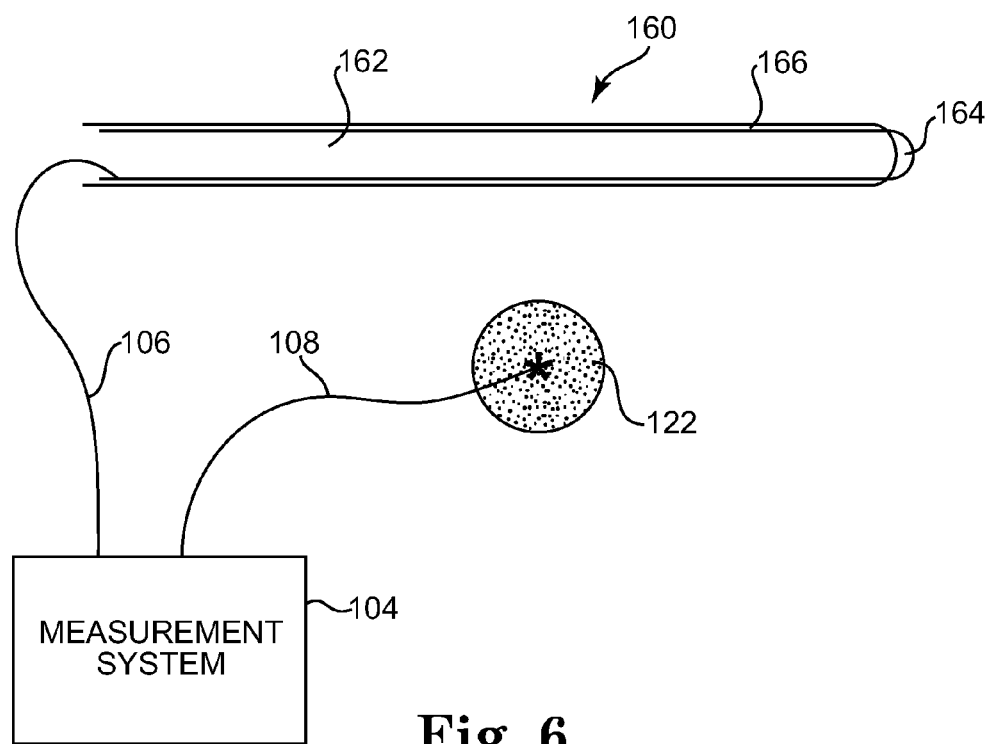
FIG. 6 is a diagram illustrating another embodiment of a tunneling tool for guiding the placement of a subcutaneous device.

FIG. 6 is a diagram illustrating another embodiment of a tunneling tool 160 for guiding the placement of a subcutaneous device. In one embodiment, tunneling tool 160 is used for tunneling tool 111 previously described and illustrated with reference to FIG. 2. In this embodiment, tunneling tool 160 includes a conductive rod 162 including a tip 164. Conductive rod 162 is coated with an insulation material 166 except at tip 164. In one embodiment, insulation material 166 includes silicon rubber or other suitable insulation material.

Tip 164 of conductive rod 162 provides a first electrode and is electrically coupled to measurement system 104 through signal path 106. A second electrode 122, for attachment to the skin of a patient, is electrically coupled to measurement system 104 through signal path 108. The impedance between tip 164 of conductive rod 162 and second electrode 122 on a patient's skin measured by measurement system 104 is different when tip 164 of tunneling tool 160 is situated within subcutaneous fat tissue than when tip 164 of tunneling tool 160 is situated within muscle tissue. A physician can monitor the measured impedance while advancing tunneling tool 160 within a patient to guide the physician in keeping tip 164 of the tunneling tool within the subcutaneous fat tissue of the patient.

Figure 7:
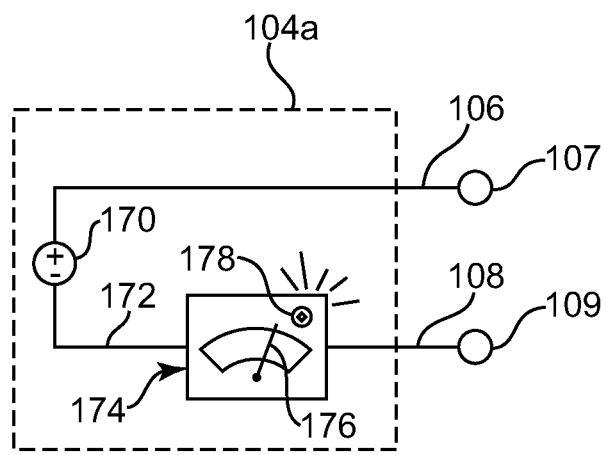
FIG. 7 is a diagram illustrating one embodiment of a measurement system.

FIG. 7 is a diagram illustrating one embodiment of a measurement system 104a. In one embodiment, measurement system 104a provides measurement system 104 previously described and illustrated with reference to FIGS. 1-6. Measurement system 104a includes a DC voltage source 170 and a meter 174. One side of DC voltage source 170 is electrically coupled to a first electrode 107 through signal path 106. In one embodiment, first electrode 107 is first electrode 132 previously described and illustrated with reference to FIGS. 3 and 4, the tip of stylet 154 previously described and illustrated with reference to FIG. 5, or tip 164 of tunneling tool 160 previously described and illustrated with reference to FIG. 6.

The other side of DC voltage source 170 is electrically coupled to one side of meter 174 through signal path 172. The other side of meter 174 is electrically coupled to a second electrode 109 through signal path 108. In one embodiment, second electrode 109 is second electrode 134 previously described and illustrated with reference to FIG. 3, second electrode 142 previously described and illustrated with reference to FIG. 4, coil 152 previously described and illustrated with reference to FIG. 5, or second electrode 122 previously described and illustrated with reference to FIG. 6.

DC voltage source 170 provides a voltage between first electrode 107 and second electrode 109. Meter 174 measures the current between first electrode 107 and second electrode 109. As the impedance between first electrode 107 and second electrode 109 increases, the current indicated by meter 174 between first electrode 107 and second electrode 109 decreases. As the impedance between first electrode 107 and second electrode 109 decreases, the current indicated by meter 174 between first electrode 107 and second electrode 109 increases. Therefore, by monitoring the current indicated by meter 174, the impedance between first electrode 107 and second electrode 109 can be measured. Based on the measured impedance, the position of the tip of a tunneling tool or lead can be determined to be within subcutaneous fat tissue or muscle tissue of a patient.

In one embodiment, meter 174 includes a needle 176 to provide a visual indication of the impedance between first electrode 107 and second electrode 109. In other embodiments, meter 174 includes other suitable visual indicators, such as a digital display, lights, etc., to provide a visual indication of the impedance between first electrode 107 and second electrode 109. In one embodiment, meter 174 includes a speaker 178 for providing an audible indication of the impedance between first electrode 107 and second electrode 109. In one embodiment, meter 174 provides a visual and/or audible indicator in response to detecting a sudden change in impedance between first electrode 107 and second electrode 109, which indicates that the tip of the tunneling tool or lead has moved from one tissue type, such as subcutaneous fat tissue, to another tissue type, such as muscle tissue.

Figure 8:
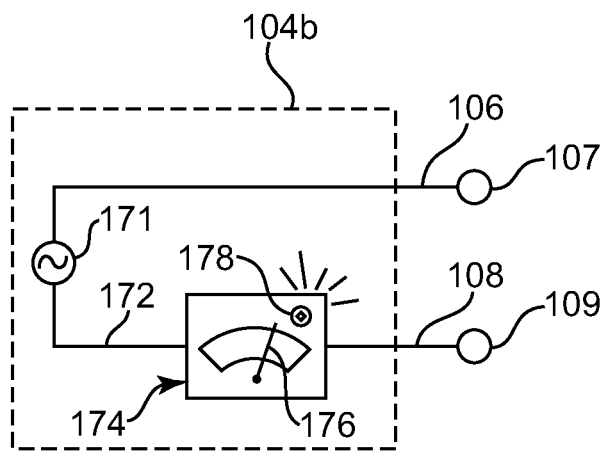
FIG. 8 is a diagram illustrating another embodiment of a measurement system.

FIG. 8 is a diagram illustrating another embodiment of a measurement system 104b. In one embodiment, measurement system 104b provides measurement system 104 previously described and illustrated with reference to FIGS. 1-6. Measurement system 104b is similar to measurement system 104a previously described and illustrated with reference to FIG. 7, except that measurement system 104b includes an AC voltage source 171 in place of DC voltage source 170. One side of AC voltage source 171 is electrically coupled to first electrode 107 through signal path 106. The other side of AC voltage source 171 is electrically coupled to one side of meter 174 through signal path 172. The other side of meter 174 is electrically coupled to second electrode 109 through signal path 108.

AC voltage source 171 provides a voltage between first electrode 107 and second electrode 109. Meter 174 measures the current between first electrode 107 and second electrode 109. As the impedance between first electrode 107 and second electrode 109 increases, the current indicated by meter 174 between first electrode 107 and second electrode 109 decreases. As the impedance between first electrode 107 and second electrode 109 decreases, the current indicated by meter 174 between first electrode 107 and second electrode 109 increases. Therefore, by monitoring the current indicated by meter 174, the impedance between first electrode 107 and second electrode 109 can be measured. Based on the measured impedance, the position of the tip of the tunneling tool or lead can be determined to be within subcutaneous fat tissue or muscle tissue of a patient.

As the frequency of AC voltage source 171 is increased, the ratio of the impedance measurement of subcutaneous fat tissue with respect to the impedance measurement of muscle tissue increases. Therefore, as the frequency of AC voltage source 171 is increased, the distinction between subcutaneous fat tissue and muscle tissue is more defined. In one embodiment, meter 174 uses the more defined distinction to provide a visual and/or audible indicator in response to detecting a sudden change in impedance between first electrode 107 and second electrode 109, which indicates that the tip of the tunneling tool or lead has moved from one tissue type, such as subcutaneous fat tissue, to another tissue type, such as muscle tissue.

Figure 9:
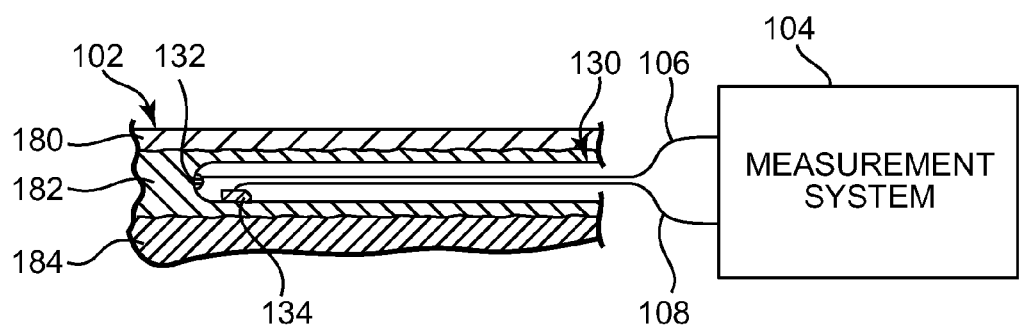
FIG. 9 illustrates a cross-sectional view of one embodiment of using a tunneling tool to place a subcutaneous device in a patient.

FIG. 9 illustrates a cross-sectional view of one embodiment of using a tunneling tool 130 to place a subcutaneous device in a patient 102. In other embodiments, tunneling tool 130 is replaced with tunneling tool 140 previously described and illustrated with reference to FIG. 4 or lead 150 previously described and illustrated with reference to FIG. 5. Tunneling tool 130 is inserted into subcutaneous fat tissue 182 between dermis 180 and muscle tissue 184 of patient 102. Measurement system 104 measures the impedance between first electrode 132 and second electrode 134. In this embodiment, measurement system 104 provides a visual and/or audible indication based on the measured impedance that the tip of tunneling tool 130 is within subcutaneous fat tissue 182. Therefore, the physician can continue to advance tunneling tool 130 to the desired location for placement of a subcutaneous device.

Figure 10:
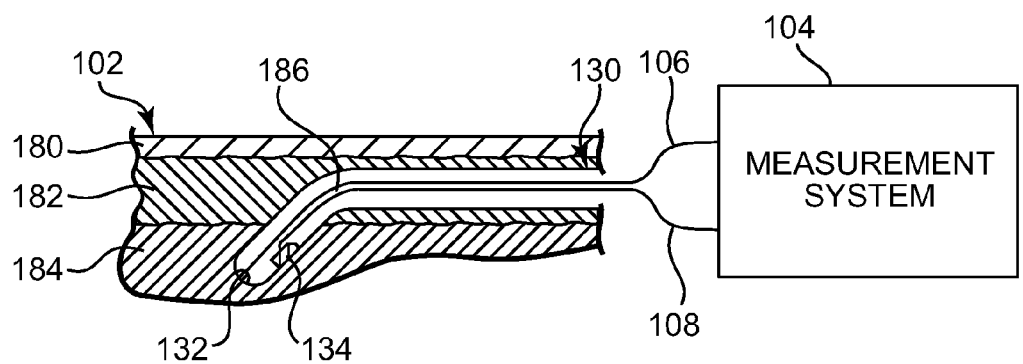
FIG. 10 illustrates a cross-sectional view of another embodiment of using a tunneling tool to place a subcutaneous device in a patient.

FIG. 10 illustrates a cross-sectional view of another embodiment of using a tunneling tool 130 to place a subcutaneous device in a patient 102. In this embodiment, tunneling tool 130 includes a bend at 186 that is pushing tunneling tool 130 into muscle tissue 184. As such, measurement system 104 measures a sudden decrease in impedance between first electrode 132 and second electrode 134 as the tip of tunneling tool 130 moves from subcutaneous fat tissue 182 to muscle tissue 184. In response to the sudden decrease in impedance, measurement system 104 provides a visual and/or audible indication that the tip of tunneling tool 130 is within muscle tissue 184. In response to the visual and/or audible indication, the physician can correct the position of tunneling tool 130 before tunneling tool 130 creates a pneumothorax.

Figure 11:
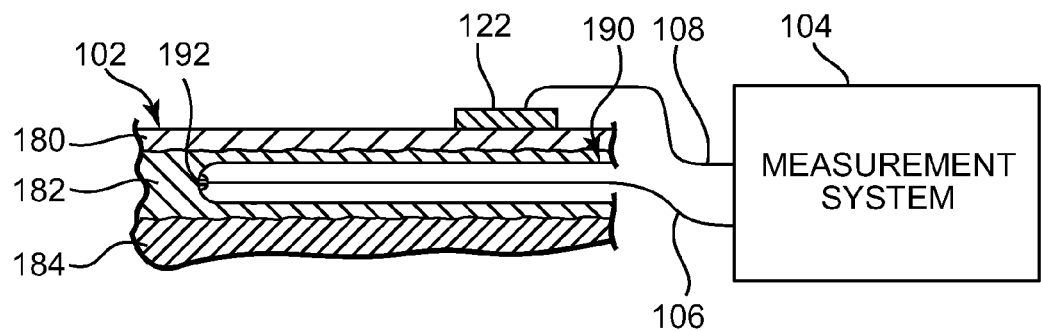
FIG. 11 illustrates a cross-sectional view of another embodiment of using a tunneling tool to place a subcutaneous device in a patient.

FIG. 11 illustrates a cross-sectional view of another embodiment of using a tunneling tool 190 to place a subcutaneous device in a patient 102. In other embodiments, tunneling tool 190 is replaced with tunneling tool 160 previously described and illustrated with reference to FIG. 6. Tunneling tool 190 includes a first electrode 192 at the distal tip of tunneling tool 190. First electrode 192 is electrically coupled to measuring system 104 through signal path 106. A second electrode 122 is attached to the patient's skin at any suitable location on the patient's body. Second electrode 122 is electrically coupled to measuring system 104 through signal path 108.

Tunneling tool 190 is inserted into subcutaneous fat tissue 182 between dermis 180 and muscle tissue 184 of patient 102. Measurement system 104 measures the impedance between first electrode 192 and second electrode 122. In this embodiment, measurement system 104 provides a visual and/or audible indication based on the measured impedance that the tip of tunneling tool 190 is within subcutaneous fat tissue 182. Therefore, the physician can continue to advance tunneling tool 190 to the desired location for placement of a subcutaneous device.

Figure 12:
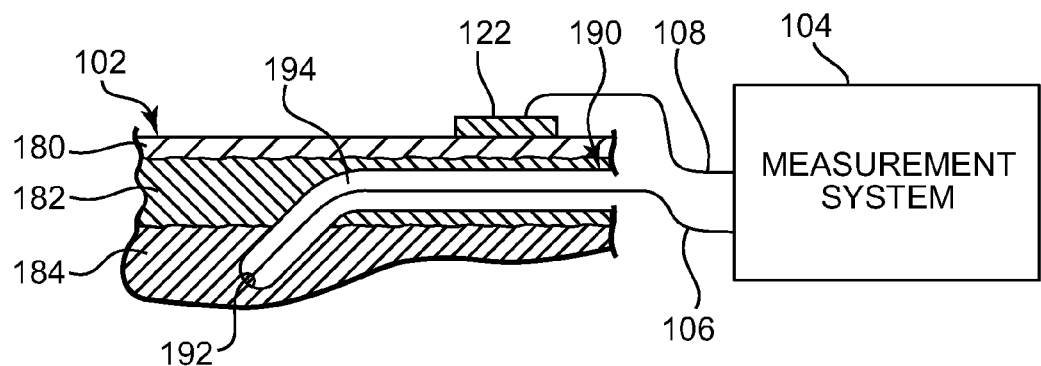
FIG. 12 illustrates a cross-sectional view of another embodiment of using a tunneling tool to place a subcutaneous device in a patient.

FIG. 12 illustrates a cross-sectional view of another embodiment of using a tunneling tool 190 to place a subcutaneous device in a patient 102. In this embodiment, tunneling tool 190 includes a bend at 194 that is pushing tunneling tool 190 into muscle tissue 184. As such, measurement system 104 measures a sudden change in impedance between first electrode 192 and second electrode 122 as the tip of tunneling tool 190 moves from subcutaneous fat tissue 182 to muscle tissue 184. In response to the sudden change in impedance, measurement system 104 provides a visual and/or audible indication that the tip of tunneling tool 190 is within muscle tissue 184. In response to the visual and/or audible indication, the physician can correct the position of tunneling tool 190 before tunneling tool 190 creates a pneumothorax.

Embodiments provide a tunneling tool for assisting a physician in the placement of a subcutaneous device, such as a coil electrode for an implantable cardioverter-defibrillator (ICD) or other suitable subcutaneous device. The tunneling tool provides an electrical guide for assisting a physician in the placement of a subcutaneous device. The electrical guide is based on impedance measurements between a first electrode at a tip of the tunneling tool and a second electrode on the tunneling tool or attached to the patient's skin. The impedance measurements indicate whether the tip of the tunneling tool is situated within subcutaneous fat tissue or within muscle tissue.

Although the present disclosure has been described with reference to preferred embodiments, workers skilled in the art will recognize that changes can be made in form and detail without departing from the spirit and scope of the present disclosure.

What is claimed is:

1. A system comprising:
   a first electrode at a tip of a tunneling tool, wherein the first electrode comprises a stylet within a central lumen of a lead;
   a second electrode attached to the tunneling tool, wherein the second electrode comprises a coil of the lead; and
   a circuit configured to determine whether the tip of the tunneling tool is within subcutaneous fat tissue or muscle tissue of a patient based on a measurement of an impedance between the first electrode and the second electrode.

2. The system of claim 1, wherein the circuit comprises an audible indicator configured to indicate whether the tip of the tunneling tool is within subcutaneous fat tissue or muscle tissue based on the impedance measurement.

3. The system of claim 1, wherein the circuit comprises a visible indicator configured to indicate whether the tip of the tunneling tool is within subcutaneous fat tissue or muscle tissue based on the impedance measurement.

4. The system of claim 1, wherein the circuit comprises a voltage source and a meter, the voltage source configured for applying a voltage across the first electrode and the second electrode, the meter configured to measure a current between the first electrode and the second electrode for measuring the impedance between the first electrode and the second electrode.

5. The system of claim 4, wherein the voltage source comprises an AC voltage source.

6. A system comprising:
   a tunneling tool including a first electrode at a tip of a tunneling tool, and a second electrode on the tunneling tool spaced from the first electrode, wherein the second electrode is a coil electrode, the tunneling tool configured to create space between the subcutaneous and muscular plane in a patient to implant a subcutaneous device;
   an impedance measurement system coupled to the first electrode and the second electrode, the impedance measurement system including a circuit configured to determine whether the tip of the tunneling tool is within subcutaneous fat tissue or muscle tissue of the patient based on a measurement of impedance between the first electrode and the second electrode.

7. The system of claim 6, wherein the tunneling tool comprises a lead system.

8. The system of claim 7, wherein the lead system includes a lead having a central lumen, and a removable stylet within the central lumen.

9. The system of claim 8, wherein the second electrode comprises a coil of the lead.

10. The system of claim 8, wherein the first electrode is located at an end of the stylet.

11. The system of claim 10, wherein the second electrode comprises a coil electrode located along the lead, and further comprising an insulation material that isolates the coil electrode from the stylet.

12. The system of claim 6, comprising:
    an implantable device positionable along the tunneling tool.

13. The system of claim 6, comprising:
    a monitor coupled to the measuring system having an indicator for indicating whether the tip of the tunneling tool is within subcutaneous fat tissue.

14. The system of claim 6, wherein the impedance measurement system includes an AC voltage source electrically coupled to at least the first electrode or the second electrode, such that a frequency of the AC voltage source may be increased for greater distinction between measurement of the subcutaneous fat tissue and muscle tissue.

15. The system of claim 14, further comprising a meter positioned between the AC voltage source and one of the first electrode or the second electrode.

16. A system comprising:
    a tunneling tool including a first electrode at a tip of a tunneling tool, and a second electrode on the tunneling tool spaced from the first electrode, the tunneling tool configured to create space between the subcutaneous and muscular plane in a patient to implant a subcutaneous device;
    an impedance measurement system coupled to the first electrode and the second electrode, the impedance measurement system including a circuit configured to determine whether the tip of the tunneling tool is within subcutaneous fat tissue or muscle tissue of the patient based on a measurement of impedance between the first electrode and the second electrode;
    wherein the tunneling tool comprises a lead system that includes a lead having a central lumen, and a removable stylet within the central lumen, wherein the first electrode is located at an end of the stylet; and wherein the second electrode comprises a coil electrode located along the lead, and further comprising an insulation material that isolates the coil electrode from the stylet; and
    wherein the impedance measurement system includes an AC voltage source electrically coupled to at least the first electrode or the second electrode, such that a frequency of the AC voltage source may be increased for greater distinction between measurement of the subcutaneous fat tissue and muscle tissue.

* * * * *